United States Patent
Stier et al.

(10) Patent No.: US 6,306,372 B1
(45) Date of Patent: Oct. 23, 2001

(54) ORAL HYGIENE COMPOSITIONS WHICH MASK THE BURN SENSATION AND THE ASTRINGENCY OF EUCALYPTOL AND ZINC

(75) Inventors: Roger E. Stier, Clifton; John Zanone, Towaco, both of NJ (US)

(73) Assignee: Noville Inc., South Hackensack, NJ (US)

( * ) Notice: Subject to any disclaimer, the term of this patent is extended or adjusted under 35 U.S.C. 154(b) by 0 days.

(21) Appl. No.: 09/598,932

(22) Filed: Jun. 21, 2000

(51) Int. Cl.$^7$ ........................................ A61K 7/16
(52) U.S. Cl. ................ 424/49; 424/58; 424/641; 424/643; 514/974
(58) Field of Search .................. 424/49–58; 514/974

(56) References Cited

U.S. PATENT DOCUMENTS

| | | | |
|---|---|---|---|
| 4,206,198 | * | 6/1980 | Schmolka ............................ 424/49 |
| 4,465,661 | * | 8/1984 | Schmolka ............................ 424/49 |
| 4,522,806 | * | 6/1985 | Muhlemann et al. .............. 424/52 |
| 4,689,214 | * | 8/1987 | Niles et al. ........................ 424/49 |
| 4,765,984 | * | 8/1988 | Vellekoop et al. ................ 424/441 |
| 4,923,685 | * | 5/1990 | Wuelknitz et al. ................ 424/49 |
| 4,945,087 | * | 7/1990 | Talwar et al. ...................... 514/60 |
| 5,292,527 | * | 3/1994 | Konopa .............................. 424/54 |
| 5,470,561 | * | 11/1995 | Klugkist et al. ................... 424/49 |
| 5,514,366 | * | 5/1996 | Diamond ............................ 424/49 |
| 5,534,243 | * | 7/1996 | Dixon et al. ....................... 424/49 |
| 5,628,986 | * | 5/1997 | Sanker et al. ...................... 424/49 |
| 5,662,888 | * | 9/1997 | Diamond ............................ 424/49 |
| 6,086,372 | * | 7/2000 | Diamond ............................ 433/216 |

FOREIGN PATENT DOCUMENTS

| | | | |
|---|---|---|---|
| 2 961 844 | * | 2/1997 | (DE) . |
| 2 961 849 | * | 2/1997 | (DE) . |
| 0 261 351 | * | 3/1988 | (EP) . |
| 0251542 A | * | 6/1988 | (EP) . |
| 0 549 027 B1 | * | 11/1995 | (EP) . |
| 0 920 857 A2 | * | 6/1999 | (EP) . |
| 2 333 540 A | * | 7/1999 | (GB) . |

* cited by examiner

Primary Examiner—Shep K. Rose
(74) Attorney, Agent, or Firm—Kenyon & Kenyon

(57) ABSTRACT

An oral hygiene composition containing eucalyptol and a zinc salt, wherein the harsh taste or burn sensation ordinarily imparted by the eucalyptol and the astringency ordinarily caused by the zinc salt are abated or eliminated by effective amounts in the composition of a taste receptor blocker, preferably in combination with a three component flavor system containing at least one spice, at least one sweetener and at least one fruity note. The taste receptor blocker is preferably a hydrogenated, ethoxylated glycerol ester which has the mouth feel characteristic of a fat but which has a much higher degree of solubility and hence improved clarity (ie., reduced cloudiness) for the composition.

33 Claims, No Drawings

ORAL HYGIENE COMPOSITIONS WHICH MASK THE BURN SENSATION AND THE ASTRINGENCY OF EUCALYPTOL AND ZINC

BACKGROUND OF THE INVENTION

1. Field of the Invention

The invention relates to mouth rinses and dentrifices which ordinarily impart a harsh taste and astringency to the mouth. More particularly, the invention relates to eucalyptol and zinc containing oral hygiene compositions wherein the burning sensation and astringency of such products is masked.

2. Description of Related Art

Mouth rinses, especially mouth washes, containing essential oils are well-known in the art of oral hygiene. For example, U.S. Pat. No. 4,945,087 is believed to be directed to the commercial product known as COOL MINT LISTERINE®. U.S. Pat. No. 4,945,087 teaches a mouth wash comprising the essential oil known as thymol which is utilized for its antimicrobial activity. The patent teaches that the thymol imparts a harsh or medicine-like taste to mouth rinses and that it would be desirable to mask this taste. For this purpose, the patent utilizes a composition containing a mixture of sugar alcohols and anethole. As an optional ingredient in the mouth rinses disclosed by U.S. Pat. No. 4,945,087, a large number of different types of surfactants are mentioned. One type of non-ionic surfactant mentioned as an optional ingredient is an ethoxylated hydrogenated castor oil (col. 4, lines 32–46), however, there is no teaching of any function of this material other than for its known function as a surface active agent (ie., surfactant). It is only through the use and manipulation of the sugar alcohols and the anethole that masking of the thymol taste is taught to be accomplished.

Another component of the commercial mouthwash LISTERINE® which is effective for its antimicrobial activity is eucalyptol (see U.S. Pat. No. 4,945,087, col. 3, lines 4–14 which discloses the possibility of using eucalyptol in addition to thymol). U.S. Pat. No. 4,945,087 attributes the harsh or medicinal taste of the product exclusively to thymol. Eucalyptol is not blamed by the patent as being responsible for or contributing to this problem. Although not appreciated or recognized by U.S. Pat. No. 4,945,807, it was subsequently discovered by the present inventors that the burning sensation of LISTERINE® is principally due to the eucalyptol, rather than the thymol. Accordingly, proposed solutions for masking the taste of thymol, such as the one taught in U.S. Patent 4,945,087, have not proved to be particularly effective for masking the burning sensation of eucalyptol containing mouth rinses such as LISTERINE®.

Another common antimicrobial agent used in oral hygiene rinses is zinc, typically added as a zinc salt. For example, European Patent Publication 0 251 542 teaches a mouth wash containing zinc chloride. However, the zinc salt is known to impart undesirable astringency to the mouth rinse. In order to abate the astringency, European Patent Publication 0 251 542 teaches the use of 0.1% to 5% by wt. polyoxyethylene hydrogenated castor oil. However, European Patent Publication 0 251 542 is not directed to eucalyptol containing mouth rinses, and the reference does not teach any means for masking the burning sensation imparted by eucalyptol containing mouth rinses.

SUMMARY OF THE INVENTION

It has been discovered that the burning sensation imparted by essential oil containing mouth rinses such as LISTERINE® is principally attributable to the eucalyptol, rather than the thymol.

Accordingly, it is an object of the invention to provide a mouth rinse composition containing eucalyptol, wherein the harsh burn taste ordinarily imparted by the eucalyptol is masked.

It is a further object of the invention to provide an oral hygiene composition containing both eucalyptol and zinc, wherein both the burn taste of the eucalyptol and the astringency of the zinc are masked.

It is another object of the invention to provide an oral hygiene composition containing both eucalyptol and zinc, wherein the composition includes a component which coats and blocks the taste receptors in the mouth so as to eliminate or reduce the burn taste and astringency of the eucalyptol and the zinc.

These and other objects of the invention which will become apparent from the following detailed description are achieved by providing an oral hygiene composition containing eucalyptol and a zinc salt, wherein the harsh taste or burn sensation ordinarily imparted by the eucalyptol and the astringency ordinarily caused by the zinc salt are abated or eliminated by effective amounts in the composition of a taste receptor blocker, preferably in combination with a three component flavor system containing at least one spice, at least one sweetener and at least one fruity note. The taste receptor blocker is preferably a hydrogenated, ethoxylated glycerol ester which has the mouth feet characteristic of a fat but which has a much higher degree of solubility and hence improved clarity (i.e., reduced cloudiness) for the composition. Although effective amounts of the taste receptor blocker and the flavor component may vary depending upon the concentrations of eucalyptol and zinc salt in the composition, generally 0.5 to 5.0% by wt. taste receptor blocker and 0.05 to 0.25% by wt. flavor component are effective.

DETAILED DESCRIPTION OF THE INVENTION

It was surprising to discover that the eucalyptol, rather than the thymol which is also typically included in mouthwash compositions for its antimicrobial properties, is primarily responsible for the burning sensation in the mouth when used.

In accordance with the invention, an oral hygiene composition, such as a mouthwash or a dentrifice, containing eucalyptol, which is effective for its antimicrobial properties but which ordinarily imparts a burning sensation to the mouth of the user, is treated with an effective amount of one or more taste receptor blockers so as to reduce or eliminate the burning sensation. The function of the taste receptor blocker is to coat the taste receptors in the mouth and thereby impede or block direct contact with the eucalyptol contained in the oral hygiene composition. A particularly effective class of compounds which can function as taste receptor blockers for the eucalyptol are hydrogenated, ethoxylated glycerol esters. These types of compounds are commercially available and may be formed in a well-known manner, namely by the ethoxylation of glycerol. The ethoxylation may be accomplished by reacting the glycerol with ethylene oxide such that hydrogen bonding to the oxygen makes the polyethylene end of the molecule more soluble. As the ethoxylation number decreases, the fat character of the molecule and hence its efficacy in coating and blocking the taste receptors increases, but the solubility usually decreases thereby decreasing clarity. If the fat characteristics of the compound are too great, solubility in the mouth rinse is adversely affected which results in an undesirable cloudiness for the product. Good solubility is essential for product clarity. Accordingly, the taste receptor blocker should be selected so as to strike the proper balance between coating efficacy on the one hand and clarity on the other.

As discussed above, the hydrogenated ethoxylated glycerol esters are prepared by, hydrogenating castor oil and treating the resulting product with from about 10 to 200) moles of ethylene glycol. The ethoxylated compounds are designated as PEG (numeral) hydrogenated castor oil in accordance with the dictionary of the Cosmetics, Toiletries and Fragrance Association, $3^{rd}$ Ed. wherein the numeral following PEG indicates the degree of ethoxylation, i.e. the number of moles of ethylene oxide added. Ethoxylation numbers in the range of from 35 to 60 have been found to provide the best results in terms of good solubility and good clarity (.e., minimal or no cloudiness). One commercially available compound which works particularly well is sold by the BASF Company under the trade name CREMOPHOR®. This compound is a hydrogenated ethoxylated castor oil. It has been found that CREMOPHOR 35 to CREMOPHOR 60 work particularly well.

The amount of taste receptor blockers incorporated in the composition will depend upon the amount of eucalyptol contained in the composition as well as the degree to which the burning sensation imparted by the eucalyptol is desired to be reduced. In the commercial mouth wash LISTERINE®, eucalyptol is typically present in an amount of about 0.07 wt. % to about 0.11 wt. %, usually between 0.08 wt. % to 0.10 wt. %. For such typical concentrations, the amount of hydrogenated, ethoxylated glycerol ester may be as low as 0.5 wt. % in order to provide a good result in terms of reducing the burning sensation. Forsuch typical eucalyptol concentrations, preferred amounts of the taste receptor blockers are from 0.5 wt. % to 5.0 wt. %. The most preferred taste receptor blocker amount is about 2.0 wt. %. The preferred amounts have been found to substantially eliminate the burning sensation without detracting from the clarity of the oral hygiene composition or adversely affecting its flavor.

In addition to eucalyptol, other additives frequently incorporated into oral hygiene compositions for their antimicrobial properties are zinc salts. The zinc salts have also been used for their tartar Control properties and are included in the commercial product tartar control LISTERINE®. Another advantage of using the taste receptor blockers in accordance with the invention is that they also have the effect of reducing or eliminating the astringency ordinarily imparted by the presence of zinc salts. Typical zinc salts which are incorporated into mouth washes and dentrifices are zinc chloride, zinc citrate, zinc acetate, zinc lactate, zinc salicylate and zinc sulphate. The amount of zinc salt present in a mouthwash is typically 0.01 wt. % to 1 wt. %, and more typically 0.02 wt. % to 0.5 wt. % in terms of zinc ion based on the total amount of the composition. For such typical amounts, the same amounts of taste receptor blocker described above which are effective for substantially reducing or eliminating the burning sensation of the eucalyptol are also effective for substantially reducing or eliminating the astringency imparted by the zinc.

The taste receptor blocker is most preferably used in combination with a flavor system containing at least one spice note, at least one sweet note and at least one fruity note. It has been found that the spice note contributes towards reducing the astringency ordinarily imparted by the zinc. The sweet note has been found to be effective in enhancing the sweetness of the system as well as reducing adverse effects (i.e. bitterness) of the eucalyptol and zinc antimicrobial actives. The fruity note also helps to reduce the residual effects of the actives. This three-component flavor system provides a sensory change in the mouth which, in combination with the taste receptor blocker, completely eliminates the burning sensation and astringency normally associated with eucalyptol-and zinc-containing oral hygiene compositions.

The spice note used in the flavor system may be selected from those spices which are commonly known, preferably ginger, clove, anise, cinnamon, nutmeg or mixtures thereof. A preferred sweet note is vanillin, especially ethyl vanillin. The fruity note may also be selected from among those known in the art, with raspberry and lemon oil being preferred. One particularly preferred flavor system for use in the invention is:

| Flavor Component Name | Formula Parts |
| --- | --- |
| Anethole USP | 370 |
| Carvone Laevo (fraction of spearmint oil) | 100 |
| Cassia Sub #418827 (cinnamon) | 100 |
| Estragole (Methyl Chavicol) | 15 |
| Ethyl Vanillin | 10 |
| Ginger Oil (BBA) N | 30 |
| Ginger Oleoresin | 25 |
| Lemon 10-Fold N (C & A) | 20 |
| Linalool Synthetic | 5 |
| Raspberry Spirit Concentrate #42000050 | 25 |
| Spearmint Terpeneless (Leman) (S) N | 300 |

The flavor system would typically be used in amounts from 0.05 wt. % to 0.25 wt. % based on the total oral hygiene composition for maximum effectiveness, depending upon the flavor one wanted to impart to the composition. Preferred amounts are from 0.1 wt. % to 0.2 wt. %, with the most preferred amount of 0.15%.

Typical oral hygiene compositions for which the present invention may be advantageously used are disclosed in U.S. Pat. No. 4,945,087 which is incorporated herein by reference. The compositions may, in addition to eucalyptol, include effective amounts of other essential oils such as those selected from the group consisting of thymol, menthol, methyl salicylate, and the like, and mixtures thereof. Generally, the total amount of essential oils present in a composition, exclusive of the thymol, can be from about 0.05 to about 0.35% by weight, based on the weight of the composition, with about 0.12 to about 0.28% by weight being preferred. For example, the compositions can contain 0.04% to 0.12% eucalyptol, 0.02% to 0.10% thymol, 0.02% to 0.07% menthol, and 0.02% to 0.09% methyl salicylate. Preferably, the eucalyptol is present in amounts of about 0.07 to about 0.11% and most preferably about 0.08 to about 0.10%; preferably thymol is present in amounts about 0.02% to 0.10% and most preferably 0.05% to 0.075%; preferably menthol is present in amounts of about 0.03% to about 0.06% by weight and most preferably about 0.04 to about 0.05%; and preferably methyl salicylate is present in amounts of about 0.03 to about 0.08% by weight and most preferably about 0.04 to about 0.07%; said % by weight being based on the total composition. In addition to these essential oils, benzoic acid is preferably present in amounts of about 0.1 to abut 0.2% by weight, based on the total composition and most preferably about 0.13 to about 0.18%.

Generally, a sugar alcohol may be present in amounts of about 20 to about 55% by weight, based on the weight of the total composition, with about 25 to about 50% by weight being preferred. Suitable amounts of anethole are usually in the range of about 0.01 to about 0.035% by weight, based on the weight of the total composition, with about 0.015 to about 0.025% by weight being preferred. The sugar alcohols that are utilizable in typical mouthwash compositions are any of those known in the art which have effective sweetening capabilities. Generally, the sugar alcohols are selected from the group consisting of sorbitol, xylitol, mannitol, maltitol, hydrogenated starch hydrolysate, and mixtures thereof. Preferably, the sugar alcohol is sorbitol.

Oral hygiene compositions containing eucalyptol and zinc, in which the burning sensation and astringency of the eucalyptol and the zinc are masked by the presence of the taste receptor blocker and the three component flavor system, include liquid oral preparations such as a mouthwash, spray or rinse. In such preparations, the vehicle—i.e. the carrier for the ingredients of the mouthwash, such as the essential oils, and the like -is typically a water-alcohol mixture. Generally, the ratio of water to alcohol is in the range of from about 1:1 to about 20:1, preferably about 3:1 to about 10:1 by weight. The total amount of water-alcohol mixture in a mouthwash preparation is typically in the range from about 50% to about 99.9% by weight of the composition. The pH value of such mouthwash preparations is generally from about 3.5 to about 8.0 and preferably from about 4 to about 7.5. A pH below 3.5 would be irritating to the oral cavity and soften tooth enamel. A pH greater than 8 would result in an unpleasant mouth feel.

Oral liquid preparations may also contain surface active agents—i.e., surfactants—in amounts up to about 5% and fluorine-providing compounds in amounts up to about 2% by weight of the preparation. Surface active agents (surfactants) are organic materials which aid in the complete dispersion of the preparation throughout the oral cavity. The organic surface active material may be anionic, non-ionic, ampholytic, or cationic and may be selected from among those well known in the art.

Fluorine providing compounds may be present in the oral preparations of this invention. These compounds may be slightly water soluble or may be fully water soluble and are characterized by their ability to release fluoride ions or fluoride containing ions in water. Typical fluorine providing compounds are inorganic fluoride salts such as soluble alkali metal, alkaline earth metal, and heavy metal salts. In an oral liquid preparation such as; a mouthwash, the fluorine providing compound is generally present in an amount sufficient to release up to about 0.15%, preferably about 0.001% to about 0.1%.

If desired, auxiliary sweeteners, in addition to those used in the three component flavor system, may be utilized in the compositions of this invention. Those sweeteners which may be included are those well known in the art, including both natural and artificial sweeteners. Without being limited to particular sweeteners, representative illustrations encompass: water-soluble sweetening agents such as monosaccharides, disaccharides and polysaccharides such as xylose, ribose, glucose (dextrose), mannose, galactose, fructose (levulose), sucrose (sugar); water-soluble artificial sweeteners such as the soluble saccharin salts, i.e. sodium or calcium saccharin salts, cyclamate salts, the sodium, ammonium or calcium salt of 3,4-dihydro-6-methyl-1,2,3-oxathiazine-4-one-2,2-dioxide; and dipeptide based sweeteners, such as L-aspartic acid derived sweeteners, such as L-aspartyl-L-phenylalanine methyl ester (aspartame). In general, an effective amount of auxiliary sweetener is utilized to provide the level of sweetness desired for particular composition, and this amount will vary with the sweetener selected. This amount will normally be 0.01% to about 40% by weight of the composition when using an easily extractable sweetener.

In addition to the spices and fruity notes contained in the special three component flavor system described above for use in conjunction with the taste receptor blocker, additional flavorings (flavoring agents) that may be used include those known to the skilled artisan, such as, natural and artificial flavors. These flavorings may be chosen from synthetic flavor oils and flavoring aromatics, and/or oils, oleo resins and extracts derived from plants, leaves, flowers, fruits and so forth, and combinations thereof. Representative flavor oils include: spearmint oil, cinnamon oil, oil of wintergreen (methyl salicylate), peppermint oil, clove oil, bay oil, eucalyptus oil, thyme oil, cedar leaf oil, oil of nutmeg, oil of sage, and oil of bitter almonds. Also, useful are artificial, natural or synthetic fruit flavors such as vanilla, and citrus oil, including lemon, orange, grape, lime and grapefruit and fruit essences including apple, pear, peach, strawberry, raspberry, cherry, plum, pineapple, apricot and so forth. These flavorings may be used individually or in admixture. Commonly used flavors include mints such as peppermint, menthol, artificial vanilla, cinnamon derivatives, and various fruit flavors, whether employed individually or in admixture.

Flavorings such as aldehydes and esters including cinnamyl acetate, cinnamaldehyde, citral, diethyllacetal, dihydrocarvyl acetate, eugenyl formate, p-methylanisole, and so forth may also be used. Generally, any flavoring or food additive such as those described in *Chemicals Used in Food Processing*, pub 1274 by the National Academy of Sciences, pages 63–258 may be used.

Further examples of aldehyde flavorings include, but are not limited to acetaldehyde (apple); benzaldehyde (cherry, almond); cinnamic aldehyde (cinnamon); citral, i.e., alpha citral (lemon, lime); neral, i.e. beta citral (lemon, lime); decanal (orange, lemon); ethyl vannillin (vanilla, cream); heliotropine, i.e. piperonal (vanilla, cream); vanillin (vanilla, cream); alpha-amyl cinnamaldehyde (spicy fruity flavors); butyraldehyde (butteir, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 2,6-dimethyl-5-heptenal, i.e. melonal (melon); 2-6-dimethyloctanal (green fruit); and 2-dodecenal (citrus, mandarin); cherry; grape; mixtures thereof; and the like.

The amount of additional flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. In general, amounts of about 0.05% to about 2.0% by weight of the compositions are useable with amounts of about 0.05% to about 1.5% being preferred.

The compositions of this invention may also contain coloring agents or colorants in amounts effective to produce the desired color. The coloring agents (colorants) uselul in the present invention, include the pigments such as titanium dioxide, which may be incorporated in amounts of up to about 2% by weight of the composition, and preferably less than about 1% by weight. Colorants may also include natural food colors and dyes suitable for food, drug and cosmetic applications.

The oral compositions of this invention may also be substantially solid or pasty in character such as a dental cream, toothpaste, or a toothpowder. Solid or pasty oral preparations contain polishing materials. Typical polishing materials are abrasive particulate materials having particle sizes of up to about 20 microns. Nonlimiting illustrative examples include; water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in toothpowder. Fortoothpaste and dental creams, the water content is about 25% to 50% by weight.

In clear gels, a polishing agent of colloidal silica and alkali metal aluminosilicate complexes are preferred since they have refractive close to the refractive indices close to the refractive indices of gelling agent liquid systems commonly used in dentrifices.

In the oral preparation that are toothpastes, dental creams, or gels the liquid vehicle may comprise water, typically in an amount of about 10–90% by weight of the composition. Polyethylene glycol, propylene glycol, glycerin or mixtures thereof may also be present as humectants or binders in amounts of about 20–25% by weight. Particularly advantageous liquid ingredients comprise mixtures of water with polyethylene glycol or glycerin and propylene glycol. A gelling agent (thickening agent) including natural or synthetic gums such as sodium carboxymethylcellulose, hydroxyethyl cellulose, methyl cellulose and the like may be used, in the range of about 0.5–5% by weight. In a toothpaste, dental cream or gel, the liquids and solids are proportioned to form a creamy or gelled mass which is extrudable from a pressurized container or from a collapsible tube.

The toothpaste or gel may also contain a surface active agent which may be an anionic, nonionic or zwitterionic detergent (surfactant) in amounts of about 0.05–5% by weight. Suitable anionic and nonionic surfactants are well known in the art. Zwitterionic surface active agents include the betaines and sulfobetaines. Typical alkyl dimethyl betaines include decyl betaine or 2-(N-decyl-N,N-dimethylammonio) acetate, coco betaine, myristyl betaine, palmityl betaine, lauryl betaine, cetyl betaine, stearyl betaine, etc. The amidobetaines similarly include cocoamidoethyl betaines, cocoamidopropyl betaine, lauramidopropyl betaine and the like. These sulfobetaines are similar in structure to the betaines, but have a sulfonate group in place of the carboxylate group, and include alkylsulfobetaines, alkylamidosulfobetaines and alkylaminosulfobetaines.

In general, the compositions of this invention are prepared utilizing techniques well known to those skilled in the art. Thus, the liquid compositions may be prepared by mixing the alcohol soluble ingredients with ethanol, adding a quantity of water to the mixture thus obtained, and then blending or mixing in the water soluble ingredients. For example, in preparing one liter of a typical liquid oral composition, thymol, eucalyptoll, menthol, methyl salicylate, anethole, surfactant, and benzoic acid are dissolved in and mixed with ethanol. To this resulting mixture a sufficient quantity of water is added, and then the auxiliary sweetener, water soluble colorants, buffers, and the like are blended in. Then additional water is added to make up one liter. Those skilled in the art will appreciate that the total amount of all ingredients (components) used in the compositions of this invention equals 100% by weight of the total composition. Also, unless stated otherwise, all percent herein are percent by weight of the total composition.

Specific preferred embodiments of the invention will now be described in the following working examples, which should be regarded in an illustrative rather than a restrictive sense.

EXAMPLE

A mouthwash having the following components was prepared:

| Ingredients | Wt. % |
| --- | --- |
| Alcohol (ethanol and essential oils thymol and eucalyptol) | 19.00 |
| Pluracare 127 (surfactant) | 0.05 |
| Flavor System (same as preferred system in specification) | 0.15 |
| CREMOPHOR 60 | 2.00 |
| Deionized water | 58.61 |
| Zinc chloride | 0.09 |
| Sorbitol 70% | 20.00 |
| Sodium Saccharin | 0.10 |
| | 100.00 |

In addition, F. D. & C. blue no. 1 was used as a colorant. In preparing the mouthwash, the zinc chloride, sodium saccharin, sorbitol and blue coloring were dissolved in the water and mixed until a clear solution was formed. Next, the CREMOPHOR was heated to a liquid and added to a separate mixture of the alcohol with essential oils, surfactant and the preferred flavor system described above. The water solution was then added to this CREMOPHOR mixture to form the mouthwash.

It was determined that the use of CREMOPHOR in this formula blocks the receptors in the tongue to mask the eucalyptol. The CREMOPHOR in combination with the flavor system also masked the negative flavor notes of the zinc, particularly dryness and astringency. The product was stable for three months at 40° C. and passed freeze thaw cycles. In addition, this product had the same bacteriocidal effects as LISTERINE®.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A composition comprising eucalyptol, an effective amount of a taste receptor blocker that is a hydrogenated ethoxylated glycerol ester which is effective to mask the burning sensation ordinarily imparted by the eucalyptol, and a flavor system which includes at least one spice note, at least one sweetener, and at least one fruity note.

2. The composition according to claim 1, wherein the taste receptor blocker is selected from the group consisting of hydrogenated ethoxylated glycerol esters.

3. The composition according to claim 1, wherein the taste receptor blocker is a hydrogenated ethoxylated glycerol ester having an ethoxylation number in the range of from 35 to 60.

4. The composition according to claim 1, wherein the taste receptor blocker has an ethoxylation number of 60.

5. The composition according to claim 1, further comprising a flavor system which includes at least one spice note, at least one sweetener and at least one fruity note.

6. The composition according to claim 1, wherein the spice note is selected from the group consisting of ginger, clove and anise; and mixtures thereof.

7. The composition according to claim 6, wherein the fruity note is selected from the group consisting of raspberry and lemon and mixtures thereof.

8. The composition according to claim 7, wherein the sweetener is vanillin.

9. The composition according to claim 7, further comprising a zinc salt.

10. The composition according to claim 6, further comprising a zinc salt.

11. The composition according to claim 6, further comprising a zinc salt.

12. The composition according to claim 1, further comprising a zinc salt.

13. The composition according to claim 1, wherein the eucalyptol is present in an amount of from about 0.04 wt. % to about 0.12 wt. % and the taste receptor blocker is present in an amount from about 0.5 wt. % to about 5.0 wt. %, wherein said percents by weight are based on the total weight of the composition.

14. The composition according to claim 13, wherein the flavor system is present in an amount from about 0.05 wt. % to about 0.25 wt. % wherein the percentages are based on the total weight of the composition.

15. The composition according to claim 14, further comprising from about 0.05 wt. % to about 2.0 wt. % of a zinc salt.

16. The composition according to claim 13, further comprising from about 0.05 wt. % to about 2.0 wt. % of a zinc salt.

17. An oral hygiene composition comprising eucalyptol, a zinc salt, an effective amount of a taste receptor blocker and an effective amount of a flavor system which includes at least one spice note selected from ginger, clove, anise, or mixtures thereof; at least one sweetener; and at least one fruity note, wherein the taste receptor blocker and flavor system are effective to mask the burning sensation of the eucalyptol and the astringency of the zinc.

18. The composition according to claim 17, wherein the taste receptor blocker is selected from the group consisting of hydrogenated ethoxylated glycerol esters.

19. The composition according to claim 17, wherein the taste receptor blocker is a hydrogenated ethoxylated glycerol ester having an ethoxylation number in the range of from 35 to 60.

20. The composition according to claim 19, wherein the taste receptor blocker is a hydrogenated ethoxylated glycerol ester having an ethoxylation number of 60.

21. The composition according to claim 17, wherein the spice note is selected from the group consisting of ginger, clove and anise and mixtures thereof.

22. The composition according to claim 17 wherein the fruity note is selected from the group consisting of raspberry and lemon and mixtures thereof.

23. The composition according to claim 17, wherein the sweetener is vanillin.

24. The composition according to claim 17, wherein the eucalyptol is present in an amount of from about 0.04 wt. % to about 0.12 wt. % and the taste receptor blocker is present in an amount from about 0.5 wt. % to about 5.0 wt. %, wherein said percents by weight are based on the total weight of the composition.

25. The composition according to claim 24 wherein the zinc salt is present in an amount of about 0.05 wt. % to about 2.0 wt. %.

26. The composition according to claim 25 wherein the flavor system is present in an amount of from about 0.05 wt. % to about 0.25 wt. %.

27. An oral hygiene composition comprising (a) about 0.02 to about 0.1% by weight of thymol;

(b) about 20 to about 55% by weight of a sugar alcohol;

(c) about 0.01 to about 0.035% by weight of anethole;

(d) about 0.04 to about 0.12% by weight of eucalyptol;

(e) about 0.02 to about 0.07% by weight of menthol;

(f) about 0.05 to about 0.25% by weight of benzoic acid;

(g) about 0.02 to about 0.09% by weight of methyl salicylate;

(h) about 5 to about 35% by weight of ethanol;

(i) about 0.05 to about 2.0% by weight of zinc salt;

(j) about 0.5 to about 5.0% by weight of a hydrogenated ethoxylated glycerol ester; and (k) about 0.05 to about 0.25% by weight of flavor system which includes at least one spice note, at least one sweetener and at least one fruity note, wherein the burning sensation of the eucalyptol and the astringency of the zinc are masked by the hydrogenated ethoxylated glycerol ester and wherein said percents by weight are based on the total weight of the composition.

28. The oral hygiene composition according to claim 27 wherein the hydrogenated ethoxylated glycerol ester has an ethoxylation number of from 35 to 60.

29. A method for masking the burning sensation of eucalyptol in an oral hygiene composition comprising the step of adding to said composition an effective amount of a taste receptor blocker that is an ethoxylated glycerol ester having an ethoxylation number in the range of from 35 to 60 and a flavor system that includes at least one spice note, at least one sweetener, and at least one fruity note.

30. The method according to claim 29, wherein the taste receptor blocker is selected from the group consisting of hydrogenated ethoxylated glycerol esters.

31. The method according to claim 29, wherein the taste receptor blocker is a hydrogenated ethoxylated glycerol ester having an ethoxylation number in the range of from 35 to 60.

32. A method for masking the burning sensation of eucalyptol and the astringency of zinc in an oral hygiene composition comprising the step of adding an effective amount of a taste receptor blocker that is an ethoxylated glycerol ester having an ethoxylation number in the range of from 35 to 60 and an effective amount of a flavor system which includes at least one spice note, at least one sweetener and at least one fruity note.

33. The method according to claim 32, wherein the taste receptor blocker is selected from the group consisting of hydrogenated ethoxylated glycerol esters.

* * * * *